(12) United States Patent
Choi et al.

(10) Patent No.: US 11,813,455 B2
(45) Date of Patent: Nov. 14, 2023

(54) MICRO DEVICE OF NERVE SIGNAL RECORDING AND STIMULATING FOR DIAGNOSIS AND TREATMENT OF CHRONIC PAIN OR ALZHEIMER'S DISEASE

(71) Applicants: Yonsei University Industry Foundation, Seoul (KR); Nformare Inc., Seoul (KR)

(72) Inventors: Heon Jin Choi, Seoul (KR); Jae Suk Sung, Seoul (KR); Youngcheol Chae, Seoul (KR)

(73) Assignees: Yonsei University Industry Foundation, Seoul (KR); Nformare Inc., Seoul (KR)

( * ) Notice: Subject to any disclaimer, the term of this patent is extended or adjusted under 35 U.S.C. 154(b) by 0 days.

(21) Appl. No.: 17/124,340

(22) Filed: Dec. 16, 2020

(65) Prior Publication Data

US 2022/0184398 A1   Jun. 16, 2022

(51) Int. Cl.
| | |
|---|---|
| *A61N 1/04* | (2006.01) |
| *A61N 1/36* | (2006.01) |
| *A61N 1/05* | (2006.01) |
| *A61N 1/378* | (2006.01) |
| *A61N 1/375* | (2006.01) |

(52) U.S. Cl.
CPC ....... *A61N 1/36082* (2013.01); *A61N 1/0551* (2013.01); *A61N 1/36062* (2017.08); *A61N 1/36071* (2013.01); *A61N 1/3754* (2013.01); *A61N 1/3787* (2013.01)

(58) Field of Classification Search
CPC ............ A61N 1/36071; A61N 1/36062; A61N 1/36082; A61N 1/0492; A61N 1/0551; A61N 1/36031; A61N 1/36025; A61N 1/36021; A61N 1/0502; A61N 1/0476
See application file for complete search history.

(56) References Cited

U.S. PATENT DOCUMENTS

| | | | |
|---|---|---|---|
| 9,248,273 B2 * | 2/2016 | Guvanasen | .............. A61B 5/24 |
| 2009/0132018 A1 * | 5/2009 | DiUbaldi | ............. A61N 1/0456 607/152 |

* cited by examiner

*Primary Examiner* — Alyssa M Alter
(74) *Attorney, Agent, or Firm* — Park, Kim & Suh, LLC

(57) ABSTRACT

Provided herein is a stimulating device being equipped with an electrode element recording and stimulating nerve signals for diagnosis and treatment of chronic pain or Alzheimer's disease and, most particularly, to a stimulating device providing electrical stimulation for chronic pain or Alzheimer's-causing proteins or measuring bio signals. The stimulating device includes a controller, a substrate being coupled to a bottom of the controller, and having a power receiving and signal delivering electrode being mounted thereon as a single body or being distinctively mounted thereon, wherein the power receiving and signal delivering electrode is capable of wirelessly receiving power and wirelessly delivering bio signals, and an electrode element being coupled to a bottom of the substrate and being capable of delivering electrical stimulation to tissues inside a body.

4 Claims, 23 Drawing Sheets

(A)  (B)

(A) Conventional (~50Hz)

5ms (B) Burst (C) 10kHz 0.1ms (A) (B)

(A)

(B)

(C)

(D)

(A)　　　　　　　　　　　　(B)

(A)    (B)

(A)  (B)

(A)  (B)

MICRO DEVICE OF NERVE SIGNAL RECORDING AND STIMULATING FOR DIAGNOSIS AND TREATMENT OF CHRONIC PAIN OR ALZHEIMER'S DISEASE

TECHNICAL FIELD

The present invention relates to a nerve signal recording and stimulating device having an electrode element and, most particularly, to using an electrode element with enhanced energy transmission efficiency so as to allow sufficient energy to be transmitted even with a small amount of applied energy by enhancing a structure of the electrode element, thereby enabling the above-mentioned device to accurately diagnose and effectively treat chronic pain or Alzheimer's disease.

BACKGROUND ART

In case persistent (or continuous) stimulation is generated during a pain transmission process, this may be developed to chronic pain. Chronic pain is characteristic in that it shows various types of pain even in stimulations below a threshold value, and patients suffering from chronic pain show pain control reactions lacking pain inhibition, as compared to healthy (or normal) people, due to the loss of pain inhibitory functions. Diseases causing chronic pain include musculoskeletal disorder, tension headache, chronic neck disorder (or pain), low back pain, conversion disorder, somatization disorder, and so on.

Most particularly, spinal cord injury may be caused by various reasons, and since such causes are very closely related to everyday life activities, a large number of patients with spinal cord injury are reported each year worldwide. Additionally, according to the Korea Spinal Cord Injury Association (KSCIA), it is estimated that patients with spinal cord injury are increasing each year in Korea. More than 75% of the patients with spinal cord injury are experiencing chronic pain, and most of the patients are experiencing pain daily and throughout the entire day. If the worst pain level is given a maximum value of 10, the pain level experienced by the patients marks an average intensity of 8.6, which is a significantly high level of pain.

Among various treatment methods for spinal cord injury, spinal cord stimulation (SCS) is a method that directly transmits electric pulses to nerves. This method is based on a principle that, since pain signals are transmitted to the cerebrum along the spinal cord, by buffering the signals being transmitted to the cerebrum, other signals may be transmitted to the cerebrum instead. A spinal cord stimulator is a type of pulse generator that can be implanted in the spine (or vertebral column), and electrical stimulation is delivered (or transmitted) to the spine through a wire that is implanted along with the stimulator. By sending electrical stimulation to a specific point where the pain is experienced from an electrode, which is a crucial component of the spinal cord stimulator, through a wire that is referred to as a lead, buffering action is exerted on the pain signals. Thus, by allowing the buffered pain signals to be transmitted to the cerebrum, the patient may experience relieved pain or may not experience any pain at all.

Meanwhile, the conventional spinal cord stimulator has the following disadvantages. Firstly, the spinal cord stimulator is installed (or implanted) at the pelvis of the patient and then a wire and a lead are extendedly installed to the affected area along the spinal cord. In this case, when the spine moves, the lead that delivers the stimulation signal from the spinal cord stimulator also moves, and this causes the patient to feel discomfort. And, occasionally, due to a poor connection state, signals may not be appropriately delivered, and, in many cases, such malfunctions can only be fixed by surgery. And, there is also a risk of disconnection. Secondly, in case of the electrodes, scars may be formed near the area of implantation. Additionally, batteries for driving the pulse generator may be damaged, and, there also lies a problem of energy efficiency being degraded over time.

Furthermore, in case of using electrodes having the shape of the related art, since pain marking a high level of pain intensity needs to be buffered by using more amplified electrical signals, a high level of electric energy shall be transmitted. However, in this case, shock may be caused to the patient's body during the process of applying such amplified power. Since there exists a high risk during its usage, it is inevitable to limit the applied power. Therefore, as a result of transmitting electrical signals with weakened (or decreased) power, the level of buffering for the pain is inevitably degraded, thereby causing the effect of pain relief to be decreased.

Therefore, a solution for improving the above-described disadvantages needs to be devised, and, accordingly, a spinal cord stimulator and other pain relieving devices for chronic pain having reinforced functions and being more convenient to use need to be developed.

Meanwhile, the Alzheimer's disease (AD) is pathologically characterized by aggregation and accumulation of neurofibrillary plaques (Alzheimer's-causing protein plaques) in the brain. Presently, various methods of approach for managing the Alzheimer's disease are being attempted. Typically, such methods include an invasive method and a non-invasive method, and, herein, representative examples of a solution for inhibiting Alzheimer's-causing protein plaques, e.g., amyloid-$\beta$ plaques from being formed, may include a method for inhibiting production of Alzheimer's-causing proteins, a method for removing Alzheimer's-causing protein fibers, aggregates, and so on. Most particularly, in case of the latter method, although it is being anticipated that Alzheimer's-causing protein immunotherapy is a most promising approach. However, similar to other protein-based drugs or medications), these therapies have metabolic instability and poor permeability through a blood-brain barrier (BBB), resulting in a failure to be assessed (or interpreted) as successful drugs for treating the Alzheimer's disease (AD).

Meanwhile, in order to address (or overcome) the limitations of such chemical therapies, the use of physical forces to modulate the aggregation state of Alzheimer's-causing proteins (i.e., A$\beta$ aggregation) has recently been attempted. Ultrasound, light, (free-electron) laser, magnetic field, direct current (tDCS), alternating current (tACS), and so on, are being applied to therapeutic solutions, and such application has been reported to reduce Alzheimer's-causing protein plaques (i.e., A$\beta$ plaques).

However, in this case, although the directionality is preferable, there may exist cases where high input energy, e.g., high power, voltage, and so on, needs to be applied for effective stimulation. And, in this case, apart from the stimulation, a high level of applied energy may be harmful to the human body. And, due to the strong aggregation abilities and aggregation propensity of the Alzheimer's-causing proteins and the heterogeneity of the aggregates, there has been difficulty in monitoring conformational change in Alzheimer's-causing proteins (i.e., Aβ peptide) under an electric field (or electric force) (EF) that is activated in real time.

DETAILED DESCRIPTION OF THE INVENTION

Technical Objects

The present invention is devised to resolve the above-described technical problems of the related art, and, therefore, a technical object of the present invention is to enhance an electrode shape so as to allow a pain relief function to be sufficiently performed by achieving high energy efficiency, even though a smaller amount of electric energy is applied.

That is, since the related art electrode generates stimulation from outside of a patient's tissue, a larger amount of power needs to be applied in order to achieve an expected electrical stimulation. However, in case of the present invention, since the present invention is implanted inside the tissue, electrical stimulation of a same level or higher may be generated with a relatively smaller amount of power.

Additionally, since the present invention requires only a small amount of power, a wireless power technology may be adopted. And, herein, since battery management is not needed, another object of the present invention is to provide a device that can be stably managed without having to experience any problems of leakage or battery damage caused during battery management.

Additionally, in the related art, even though a specific signal is generated, a flat-type electrode detects the generated specific signal as a type of ensemble signal. On the other hand, the present invention allows the electrode to detect a more segmented specific signal as it is. Thus, another object of the present invention is to enable a signal to be precisely adjusted according to a disease or pain, or to allow a level of disease or pain to be more accurately determined.

Additionally, by performing stimulation and recording at the same time, another object of the present invention is to allow early treatment to be carried out on chronic pain by consistently detecting nerve signals and applying electrical stimulation whenever an anomaly signal is detected, and, conversely, to observe prognosis after treatment by detecting changes in nerve signals after applying electrical stimulation.

Additionally, by being coupled with a storage device, another object of the present invention is to allow big data on bio signals that are accumulated during the management process of the device to be collected and stored, thereby optimizing a stimulation protocol through a deep learning process based on the collected and stored big data.

Additionally, since compactization of the device may be achieved, another object of the present invention is to minimize tissue damage when performing an implant inside the patient's body and to reduce burden on the patient.

Additionally, another object of the present invention is to allow energy that is needed for electric or magnetic stimulation to be locally selected and concentrated by adjusting the structure of an electrode or coil that is needed for the electric or magnetic stimulation.

Additionally, another object of the present invention is to adjust a size and area of energy needed for electric or magnetic stimulation by adjusting the structure of an electrode or coil that is needed for the electric or magnetic stimulation.

Finally, another object of the present invention is to observe (or monitor) molecular conformational change in Alzheimer's-causing proteins (i.e., Aβ peptide) in real time by being directly installed within a cell and providing sufficient folding free energy that is needed for disintegration (or disaggregation) of Alzheimer's-causing protein aggregates (i.e., Aβ aggregates) under a low-voltage condition.

Technical Solutions

In order to achieve the above-described objects of the present invention, provided herein is a stimulating device being equipped with an electrode element recording and stimulating nerve signals for diagnosis and treatment of chronic pain or Alzheimer's disease, wherein the stimulating device provides electrical stimulation for chronic pain or Alzheimer's-causing proteins or measures bio signals. The stimulating device may include a controller, a substrate being coupled to a bottom of the controller, and having a power receiving and signal delivering electrode being mounted thereon as a single body or being distinctively mounted thereon, wherein the power receiving and signal delivering electrode is capable of wirelessly receiving power and wirelessly delivering bio signals, and an electrode element being coupled to a bottom of the substrate and being capable of delivering electrical stimulation to tissues inside a body.

It is preferable that the electrode element includes a base substrate, and at least one pillar-type electrode part protruding from the base substrate, a flat-type electrode part having an insulation coating layer processed to have multiple holes implemented thereon, or a coil-type electrode part. Herein, in case the electrode part is a pillar-type, a non-conductive coating layer may be included in at least part of the electrode part excluding edge portions of the electrode or an upper part of the base substrate, and, in case the electrode part is a coil-type, a through hole may be formed at a center part, and at least one conductive plate having at least one slit extending outward from the through hole may be deposited to be spaced apart from the electrode part.

It is preferable that, in case the electrode part is a pillar-type, among bottom parts of the electrode part, a feeding is formed in a region where at least one bottom part of the pillar-type electrode part is embedded in the base substrate.

It is preferable that, in case the electrode part is a pillar-type, an edge portion of the electrode part and part of side surfaces extending from the edge portion are exposed.

It is preferable that, in case two or more conductive plates exist, the conductive plate is deposited so as to allow a position of a slit on each conductive layer to be varied.

It is preferable that the substrate is distinguished as a substrate including a power receiving electrode capable of wirelessly receiving power, and a substrate including a signal transmitting electrode capable of wirelessly delivering bio signals.

Effects of the Invention

According to the present invention, by enhancing an electrode shape, expected herein is an effect of allowing a pain relief function to be sufficiently performed by achieving high energy efficiency, even though a smaller amount of electric energy is applied.

Additionally, since the present invention requires only a small amount of power, a wireless power technology may be adopted. And, herein, since battery management is not needed, expected herein is an effect of allowing a device to be stably managed without having to experience any problems of leakage or battery damage caused during battery management.

Additionally, in the related art, even though a specific signal is generated, a flat-type electrode detects the generated specific signal as a type of ensemble signal. On the other hand, the present invention allows the electrode to detect a more segmented specific signal as it is. Thus, expected herein is an effect of enabling a signal to be precisely adjusted according to a disease or pain, or allowing a level of disease or pain to be more accurately determined.

Additionally, by performing stimulation and recording at the same time, expected herein is an effect of allowing early treatment to be carried out on chronic pain by consistently detecting nerve signals and applying electrical stimulation whenever an anomaly signal is detected, and, conversely, observing prognosis after treatment by detecting changes in nerve signals after applying electrical stimulation.

Additionally, by being coupled with a storage device, expected herein is an effect of allowing big data on bio signals that are accumulated during the management process of the device to be collected and stored, thereby optimizing a stimulation protocol through a deep learning process based on the collected and stored big data.

Additionally, since compactization of the device may be achieved, expected herein is an effect of minimizing tissue damage when performing an implant inside the patient's body and to reduce burden on the patient.

Additionally, expected herein is an effect of allowing energy that is needed for electric or magnetic stimulation to be locally selected and concentrated by adjusting the structure of an electrode or coil that is needed for the electric or magnetic stimulation.

Additionally, expected herein is an effect of adjusting a size and area of energy needed for electric or magnetic stimulation by adjusting the structure of an electrode or coil that is needed for the electric or magnetic stimulation.

Finally, expected herein is an effect of observing (or monitoring) molecular conformational change in Alzheimer's-causing proteins (i.e., Aβ peptide) in real time by being directly installed within a cell and providing sufficient folding free energy that is needed for disintegration of Alzheimer's-causing protein aggregates (i.e., Aβ aggregates) under a low-voltage condition.

MODE FOR CARRYING OUT THE INVENTION

Figure 1:
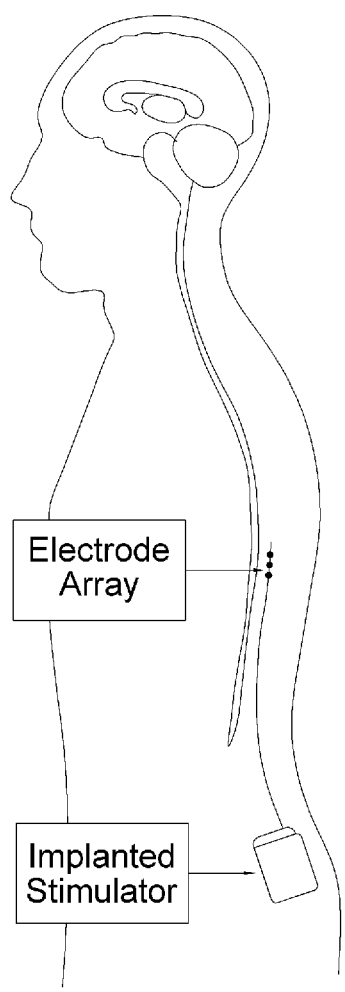
FIG. 1 is a mimetic diagram showing an installation state of a related art spinal cord stimulator.

Hereinafter, in order to allow anyone with ordinary knowledge and skills in the art to easily carry out the present invention, exemplary embodiments of the present invention will be described in detail with reference to the appended drawings. However, the present invention may be implemented in various forms and shall not be limited only to the exemplary embodiments described herein. Additionally, in the appended drawings, for clarity in the description of the present invention, parts that are not related to the description of the present invention have been omitted from the drawings, and, throughout the entire specification, similar parts have been assigned with similar reference numerals.

Throughout the entire specification, it shall be understood that, when a particular part is said to "include" a particular component, unless specified otherwise, this means that other components may be further included and does not mean that other components are excluded.

Furthermore, terms such as " . . . unit", " . . . part", and so on, means a unit performing or processing at least one function or operation.

<Chronic Pain>

In this description, although a spinal cord stimulator (100) for diagnosing and treating pain occurring in the spine has been given as an example and described accordingly, the stimulator (100) according to the present invention may also be used for the purpose of diagnosing and treating various types of pain in addition to stimulating the spinal cord. And, therefore, as long as the stimulator (100) according to the present invention is implantable, the area of application will not be limited.

FIG. 1 is a mimetic diagram showing an installation state of a related art spinal cord stimulator (100). As shown in the drawing, the related art spinal cord stimulator (100) is generally configured to have a planar (or flat) form, the (electric) stimulator being equipped with a battery is then implanted inside the body, e.g., in the hip. Thereafter, an electrode being wired (or connected by wire) to the stimulator is installed to be located near the affected area of the spine.

That is, the related art spinal cord stimulator (100) is different from the spinal cord stimulator according to the present invention in that the spinal cord stimulator (100) is located outside the spine instead of being inserted inside the spinal cord. Therefore, for effective stimulation, if possible, high input power is needed. However, as the input power value becomes higher, this may act as a burden on the patient's body, thereby causing tissue damage in some occasions. Therefore, a solution for resolving such problem is needed.

Figure 2:
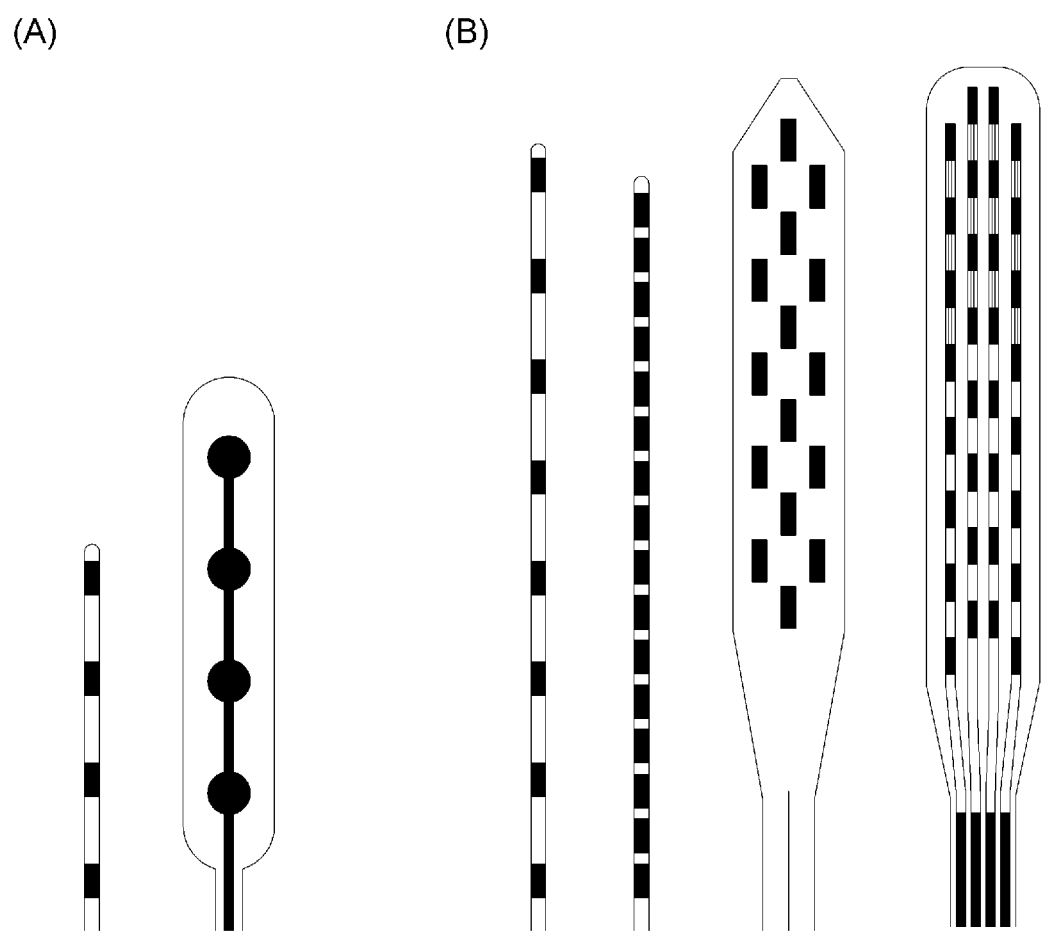
FIG. 2 is a mimetic diagram showing various forms of a related art spinal cord stimulator.
Figure 3:
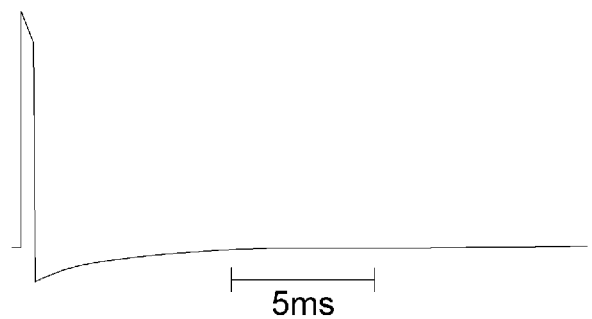
FIG. 3 is a diagram showing waveforms being generated from a related art spinal cord stimulator.
Figure 3:
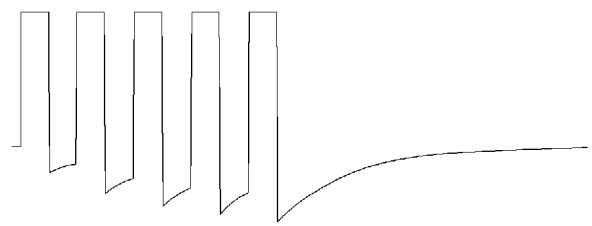
Figure 3:
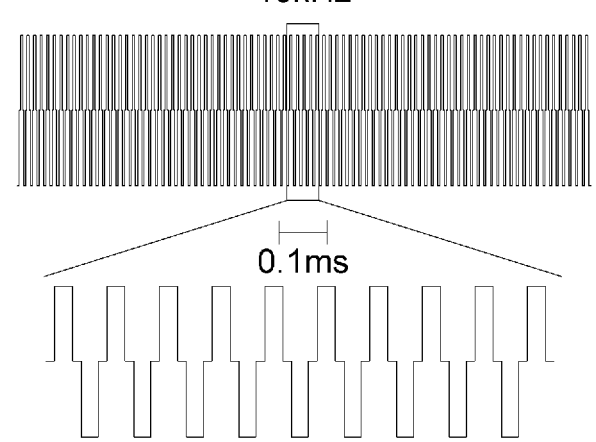

The related art spinal cord stimulator (100) has been developed in various forms, as shown in FIG. 2. Additionally, FIG. 3 is a diagram showing waveforms being generated from a related art spinal cord stimulator (100), and, herein, the waveforms are mostly periodic waves.

Figure 4:
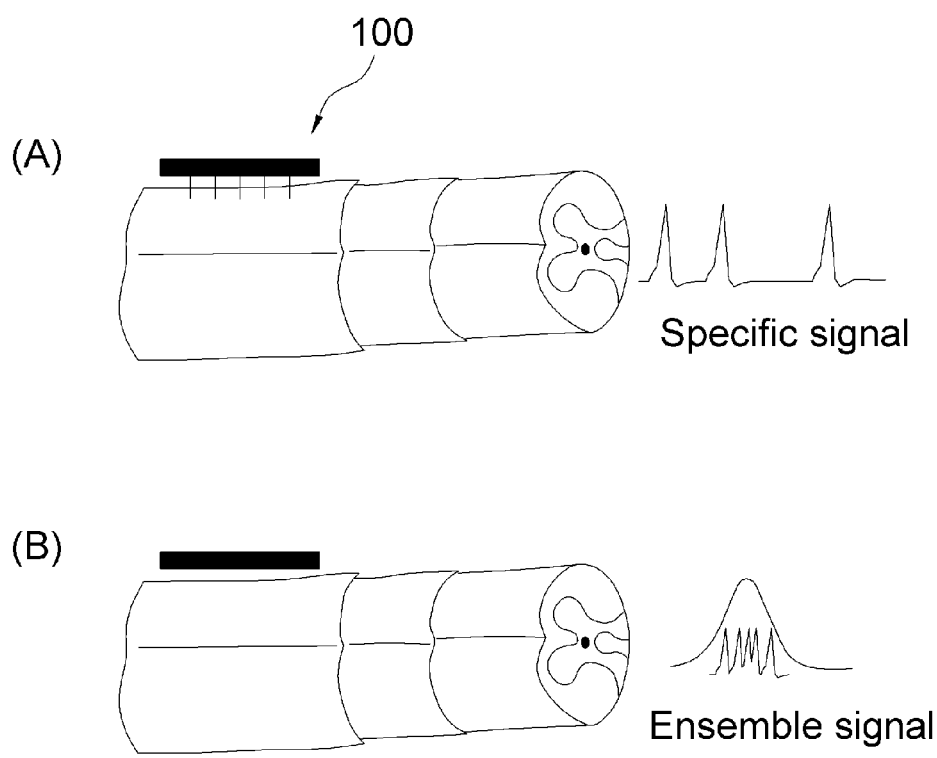
FIG. 4 is a mimetic diagram showing an installation state of a related art spinal cord stimulator and a spinal cord stimulator according to the present invention.

FIG. 4 is a mimetic diagram showing an installation state of a related art spinal cord stimulator (100) and a spinal cord stimulator (100) according to the present invention. As shown in the drawing, the related art spinal cord stimulator (100) delivers periodic wave via ensemble signal, whereas the spinal cord stimulator (100) according to the present invention delivers a specific signal according to electrode forms, intervals between the electrodes, and so on. Therefore, the spinal cord stimulator (100) according to the present invention is advantageous in that precise adjustment of the signals is possible according to the disease or pain, or that the level of the disease or pain may be more accurately determined.

Herein, in case pain occurs, electrical stimulation is performed through an electrode so that stimulation can be applied to the corresponding part. Herein, the amount of energy performing the stimulation is monitored, and the monitored amount of energy is dataficated (i.e., transformed or processed to data). In case the pain is not completely relieved, the amount of applied energy may be adjusted. By matching the adjusted amount of applied energy with a bio signal corresponding to the nerve part, matching data may be obtained, and, later on, such data may be generated into a platform that is needed for managing a stimulator for enhancing relief of chronic pain.

Herein, a specific signal refers to a signal being sent, as a bio signal, from an affected area for diagnosis. This is also referred to as an action potential. This may be defined as an analog-type bio signal that is generated by a nerve stimulation being delivered from a nerve cell, which is referred to as a neuron.

Figure 5:
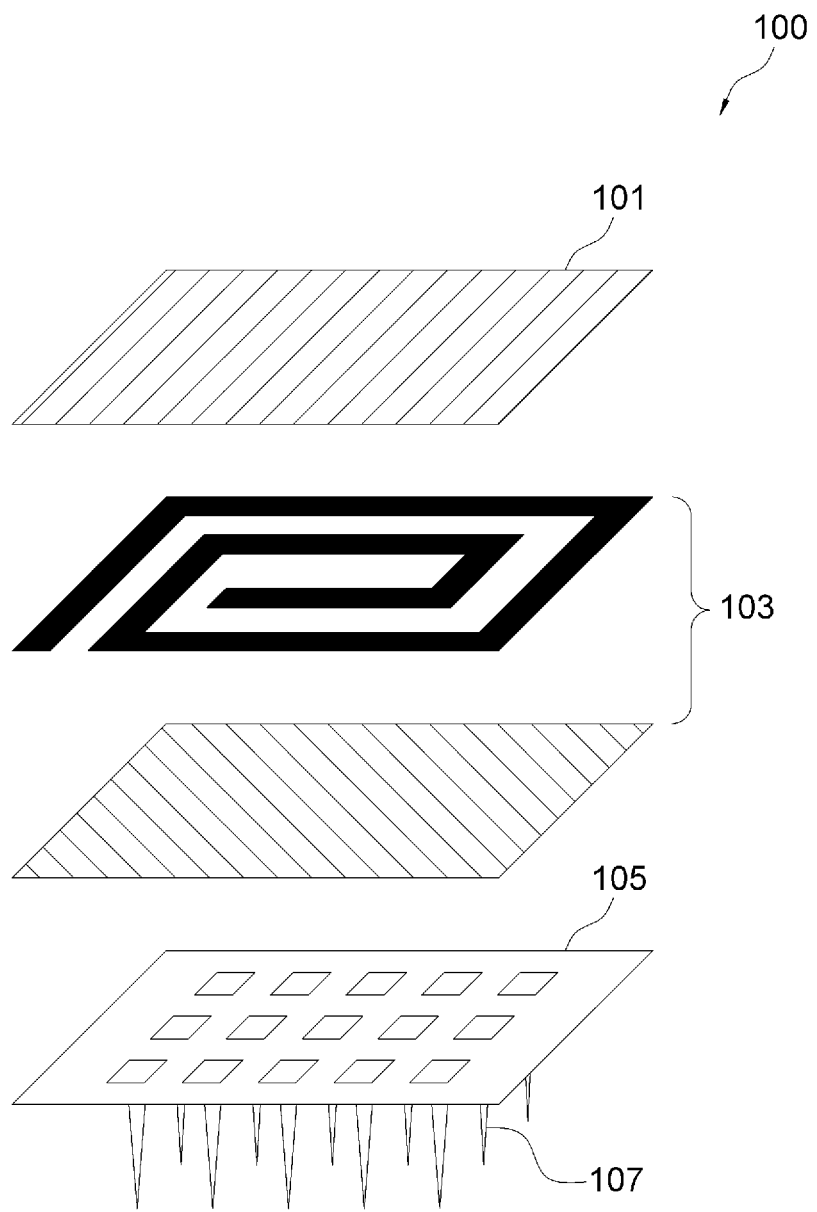
FIG. 5 is an exploded perspective diagram showing a spinal cord stimulator according to an embodiment of the present invention.

FIG. 5 is an exploded perspective diagram showing a spinal cord stimulator (100) according to an embodiment of the present invention. As shown in the drawing, the spinal cord stimulator (100) according to the present invention provides electrical stimulation for chronic pain or Alzheimer's-causing proteins or measures bio signals. Herein, the spinal cord stimulator (100) according to the present invention includes a controller (101), a substrate (103) being coupled to a bottom of the controller (101), and having a power receiving and signal delivering electrode being mounted thereon as a single body or being distinctively mounted thereon, wherein the power receiving and signal delivering electrode is capable of wirelessly receiving power and wirelessly delivering bio signals, and an electrode element being coupled to a bottom of the substrate (103) and being capable of delivering electrical stimulation to tissues inside a body.

Meanwhile, the substrate (103) may functionally operate as a single body, as described above. However, as another type, the substrate (103) may also be distinguished as a substrate (103) including a power receiving electrode that is capable of wirelessly receiving power, and a substrate (103) including a signal transmitting electrode that is capable of wirelessly delivering bio signals. That is, each of the substrate (103) having the function of receiving power and the substrate (103) having the function of delivering signals is mounted on the spinal cord stimulator so as to be operated individually as separate modules.

Herein, the electrode element may include a base substrate (105), an electrode part (107) being formed as at least one pillar-type parts protruding from the base substrate (105), as a flat-type part having an insulation coating layer implemented thereon, wherein the insulation coating layer has multiple holes (115) formed thereon, or as a coil-type part, and a connecting part being formed in a region where the electrode part (107) and the base substrate (105) are connected so as to receive signals or power and to deliver signals.

One of the main characteristics of the present invention is the electrode part (107), and the role of the electrode part (107) is to enable electrical stimulation to be efficiently performed for a low input power or an adequate level of input power that can be tolerated by a patient's body. For this, various forms of electrode units (107) have been devised as described below.

Firstly, in a pillar-type electrode, by forming a non-conductive coating layer (109) on at least the electrode part (107) or base substrate (105), excluding the upper part of the pillar-type electrode, an electric field (or electric force) may be optionally generated with high intensity (or force) from the exposed area of the electrode on which the non-conductive coating layer (109) is not formed. Thus, the electrical stimulation may be precisely performed according to the rules of selection and concentration.

Secondly, a non-conductive coating layer (109) is formed on a related flat-type electrode. Herein, by locally performing hole-processing so that a surface of the electrode can be exposed, an electric field may be generated from the corresponding hole (115). Thus, the flat-type electrode may perform similar functions as the pillar-type electrode.

Thirdly, in case of a coil-type electrode, the electrode part (107) is configured by depositing a conductive plate (119) so as to be spaced apart from the electrode. At this point, a hole (115) is formed at a center of the electrode plate, and a slit (123) is formed to extend from the hole (115) along a specific direction of the conductive plate (119). Thus, a magnetic field is formed through the hole (115) and the slit (123) by the power being supplied from the coil-type electrode.

The aforementioned electric field and magnetic field become the energy that is needed for the electrical and magnetic stimulation, which is the object of the stimulator (or stimulating device) (100) according to the present invention. Such stimulation may be performed with more precision and accuracy, and the level of pain, location of the affected area, and so on, may also be assessed and determined with more precision.

Figure 6:
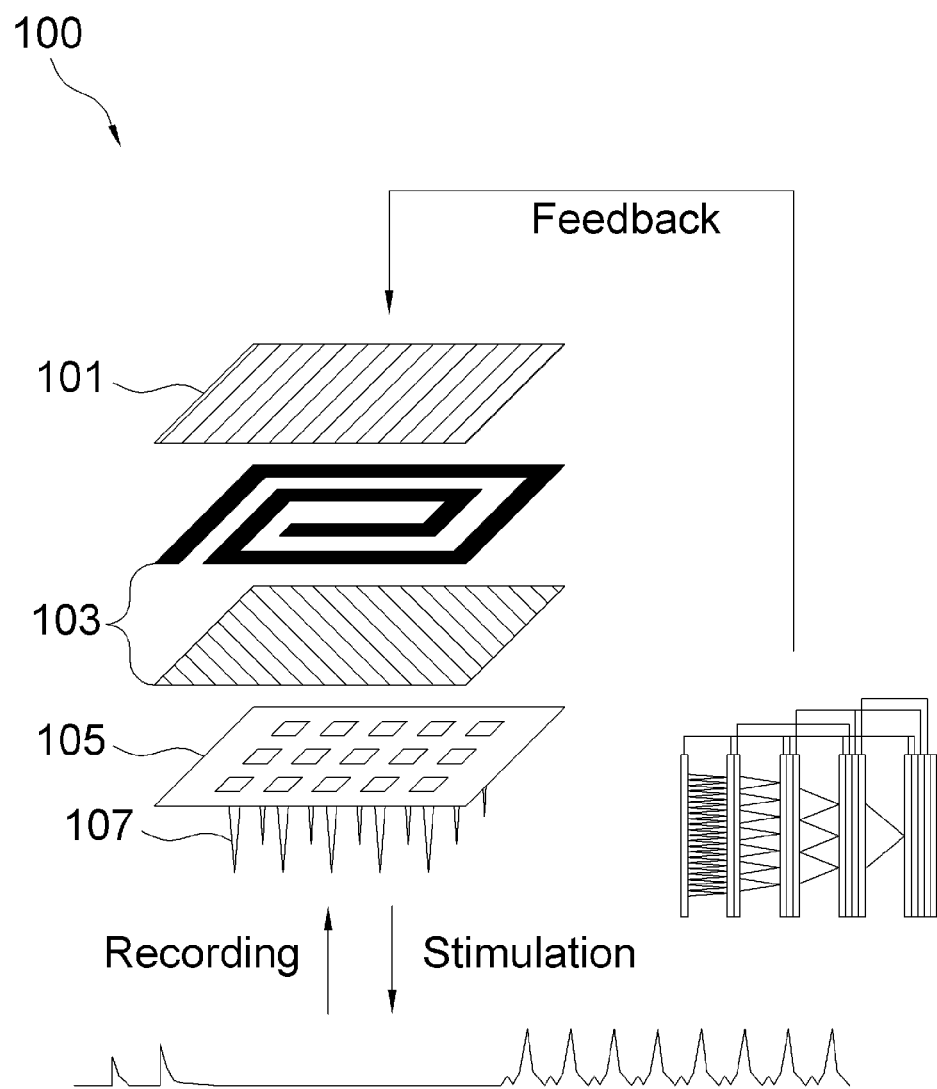
FIG. 6 is a behavioral diagram of the spinal cord stimulator shown in FIG. 5.

FIG. 6 is a behavioral diagram of the spinal cord stimulator (100) shown in FIG. 5. As shown in the drawing, the stimulator (100) according to the present invention generates stimulation, receives results obtained by the generated stimulation, and records the received results. Thereafter, the stimulator (100) may be controlled to generate new appropriate stimulation based on the recorded results. When the results are accumulated, the accumulated results may then be used as big data, which may contribute to the enhancement of devices and methods for operating and managing such devices in order to derive more improved and enhanced treatment effects.

Figure 7:
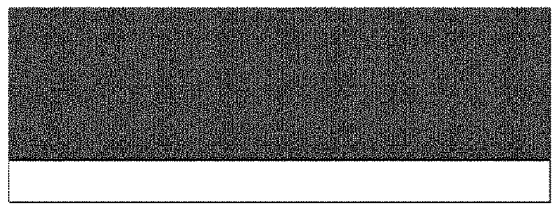
FIG. 7 are electric field distribution charts shown when applying a related art spinal cord stimulator and a spinal cord stimulator according to the present invention, respectively.
Figure 7:
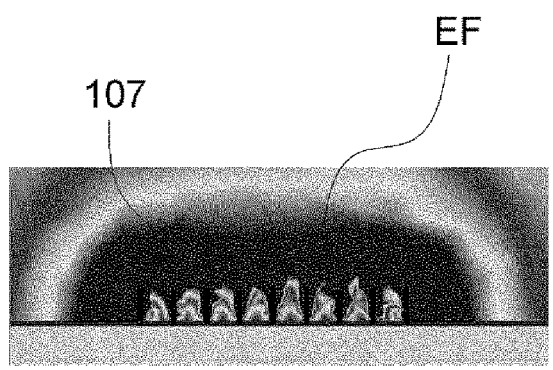

FIG. 7 are electric field distribution charts shown when applying a related art spinal cord stimulator (100) and a spinal cord stimulator (100) according to an embodiment of the present invention, respectively. As shown in the drawing, in the related art spinal cord stimulator (100), the intensity of the electric field is low, and the electric field is distributed without any particular characteristic. And, in case of the spinal cord stimulator (100) according to the present invention, it may be verified that a high-density electric field can be formed mostly around the electrode.

Figure 8:
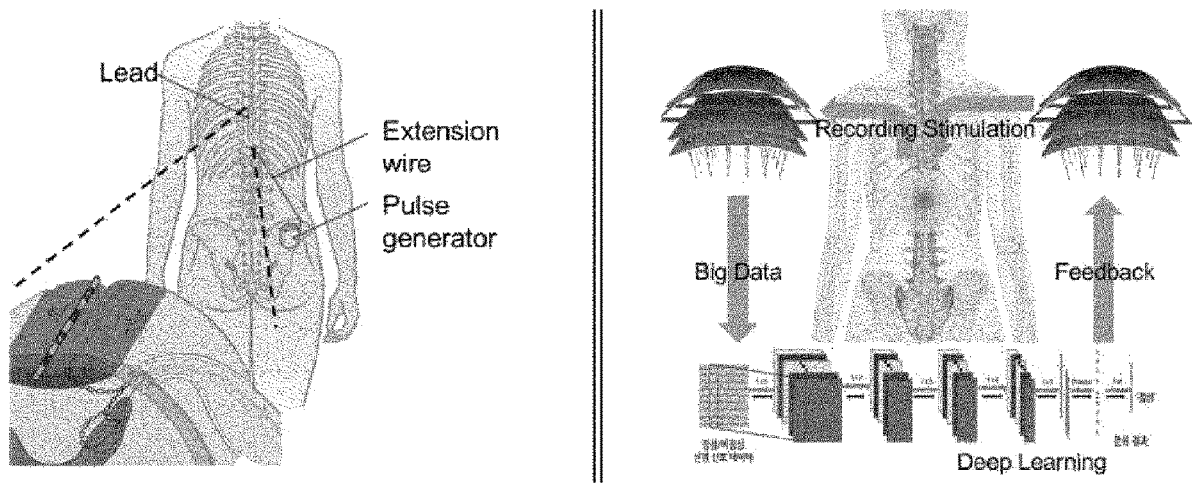
FIG. 8 is a mimetic diagram showing exemplary installation states of a spinal cord stimulator according to the present invention and a related art spinal cord stimulator both being installed inside a human body.

FIG. 8 is a mimetic diagram showing exemplary installation states of a spinal cord stimulator (100) according to the present invention and a related art spinal cord stimulator (100) both being installed inside a human body. As shown in the drawing, the present invention may be directly implanted in the spine, thereby being capable of delivering stimulation with more precision. The present invention may also operate and manage the stimulator (100) based on feedback provided through deep learning after obtaining big data. This feature differentiates the stimulator (100) according to the present invention from the related art spinal cord stimulator (100), which merely provides stimulation.

Hereinafter, it will be described in detail that a concentration effect of the electric field or magnetic field may be derived through various shape adjustments of the electrode part (107) in the electrode element according to the present invention. Accordingly, a stimulator (100) that can be effectively applied to various types of chronic pain may be fabricated from various shape adjustments of the electrode part.

Figure 9:
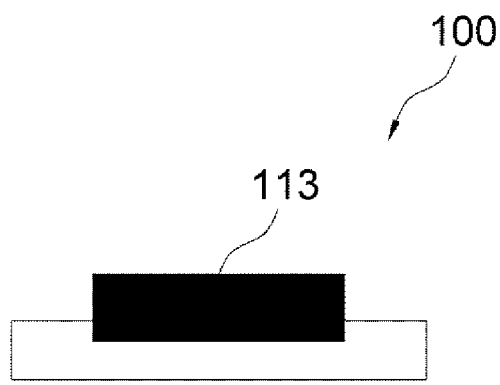
FIG. 9 is a diagram showing distribution and direction of an electric field being generated from an electrode having a shape of the related art.
Figure 9:
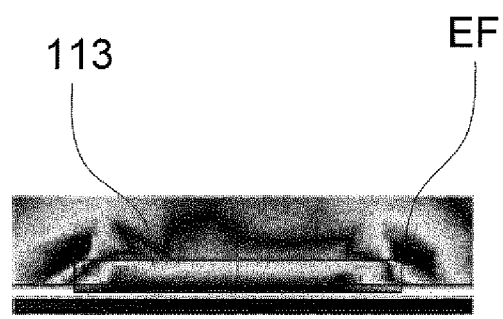
Figure 9:
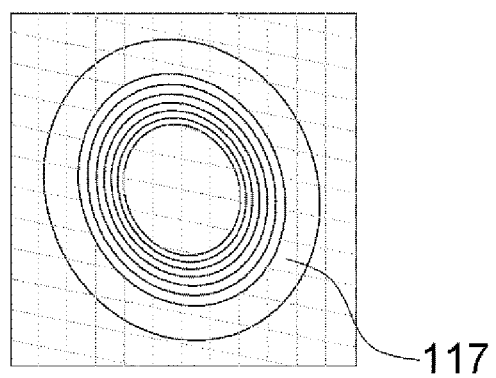
Figure 9:
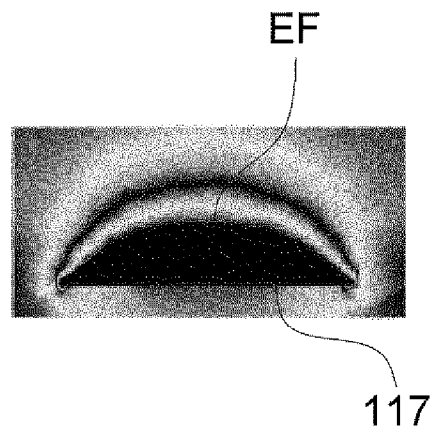

FIG. 9 is a diagram showing distribution and direction of an electric field being generated from an electrode having a shape of the related art. And, FIG. 10 is a diagram showing an electric field distribution from a pillar-type electrode according to an embodiment of the present invention.

As shown in FIG. 9, the electrode having the related art shape is a flat structured electrode or a simple coil-type electrode. In case of the former, it may be verified that the electric field is generated intensely at corner regions of the electrode and not its flat surface (or planar) area. This is because the electric field tends to gather in regions of a metallic surface having little curvature, and this is a general phenomenon that occurs in all general types of electrodes. Therefore, in order to form an intense electric field on the flat surface region, which occupies most of the surface of the electrode, a significantly high level of voltage needs to be applied. And, at this point, since an unwanted intense electric field is locally formed at corner regions of the electrode, this leads to an uneven distribution of the electric field. And, evidently, if this is applied to a patient's body, tissue damage may occur due to the intense electric field. Therefore, there may exist a critical risk in the usage of the flat-type electrode.

In case of the latter, as an embodiment, a loop antenna coil-type electrode for forming an electric field and an electric field formed by the electrode may be verified. Generally, at this point, the distribution of the electric field shows a maximum level of electric field at a center part of the coil and reduced levels of electric field nearing the end part of the coil. The electric field is formed only on the upper surface and not on the bottom surface because, when forming the coil electrode, a magnetic substance for shielding (or blocking) the electric field was positioned on the bottom surface.

Figure 10:
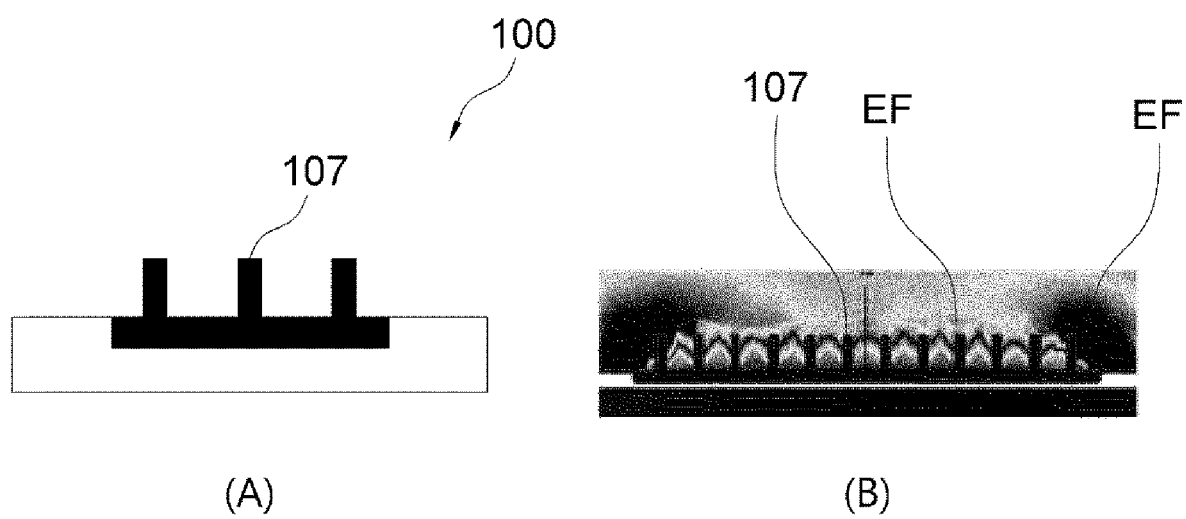
FIG. 10 is a diagram showing an electric field distribution from a pillar-type electrode according to an embodiment of the present invention.

Meanwhile, as shown in FIG. 10, in case of adopting the pillar structure to the electrode, since part of the field is also formed on inner parts of the electrode, as compared to the flat-structured electrode, it is apparent that a more even field distribution is achieved. However, results show that the electric field is still not appropriately formed at the center part of the electrode.

Figure 11:
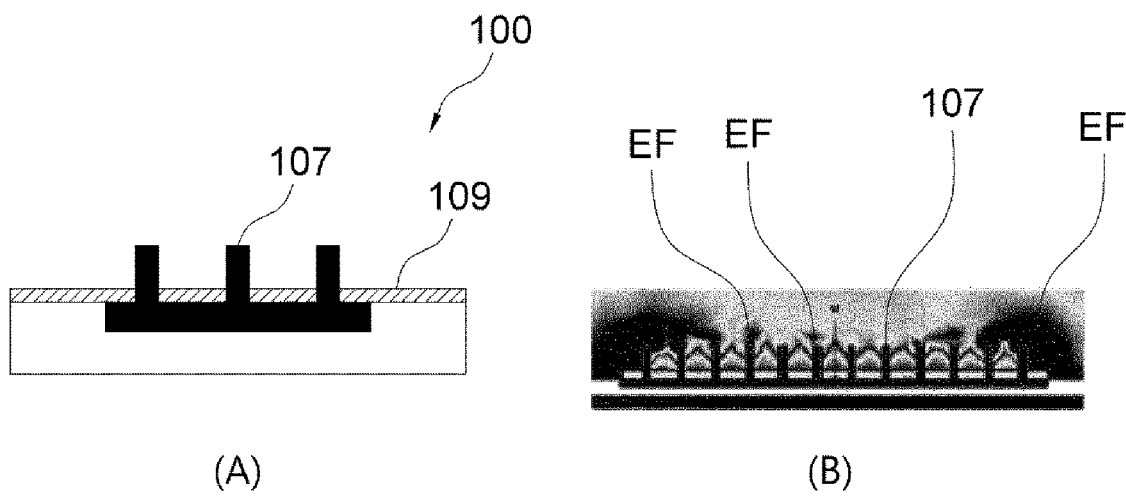
FIG. 11 is a diagram showing a non-conductive coating layer formed on a base substrate including a lower part of a pillar-type electrode and an electric field distribution according to this structure.

In case the electrode part (107) according to the present invention is a pillar-type electrode part (107), FIG. 11 is a diagram showing a non-conductive coating layer (109) formed on a base substrate (105) including a lower part of a pillar-type electrode part (107) and an electric field distribution according to this structure.

As shown in the drawing, it is apparent that part of the electric field is being more distinctly formed as compared to FIG. 10. Thus, as compared to the conventional pillar-type electrode part (107), each pillar-type electrode part (107) may deliver higher electric field energy. This is also shown in FIG. 12, wherein it can be verified that the electric field is formed in each pillar-type electrode part (107), which is similar to the results shown in FIG. 11.

Figure 12:
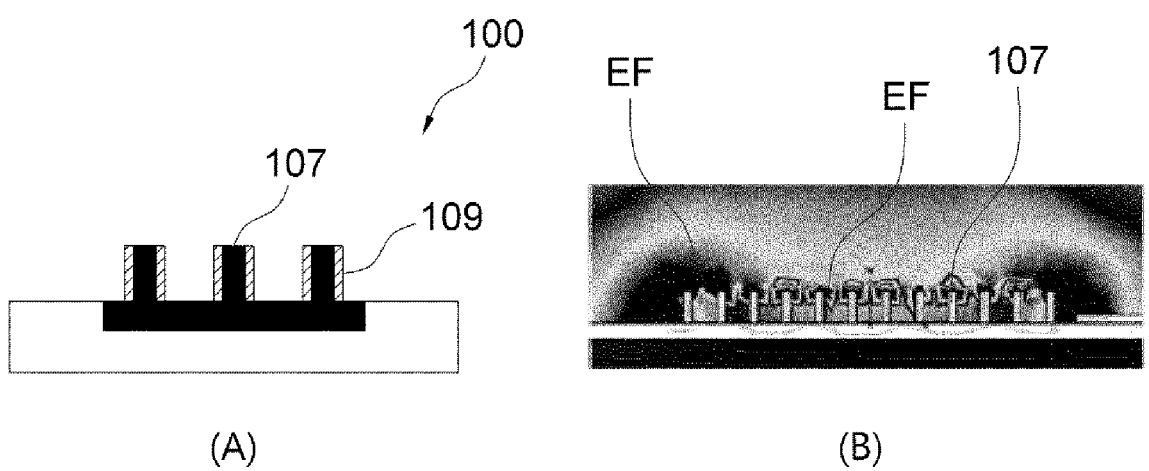
FIG. 12 is a diagram showing a non-conductive coating layer formed on a pillar-type electrode excluding an upper part of the pillar-type electrode and an electric field distribution according to this structure.
Figure 13:
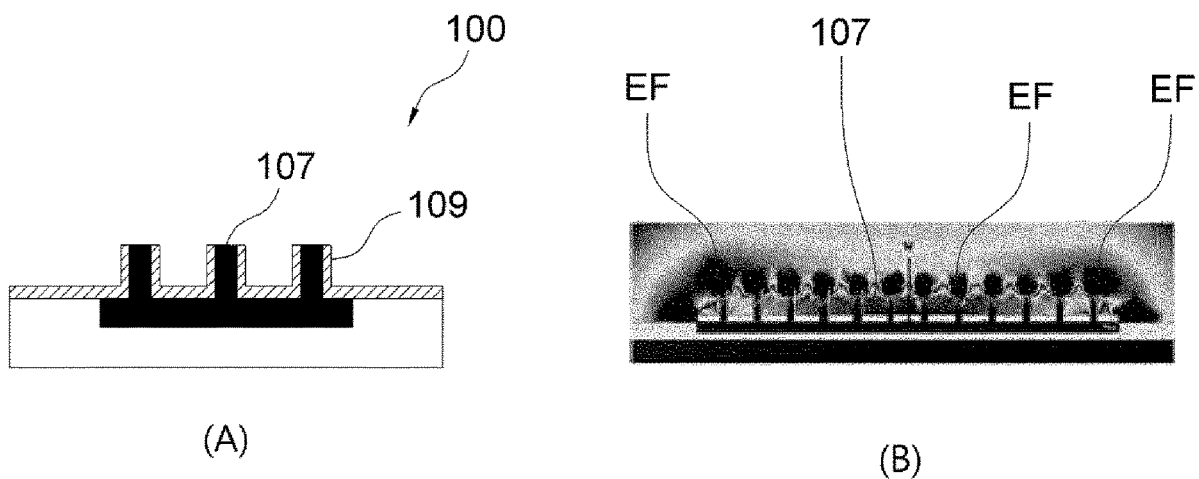
FIG. 13 is a diagram showing a combination of FIG. 11 and FIG. 12.

FIG. 13 is a diagram showing a combination of FIG. 11 and FIG. 12. Herein, a non-conductive coating layer (109) is formed on both side surfaces of the pillar-type electrode and on an upper surface of the base substrate (105). As compared to FIG. 11 and FIG. 12, it is apparent that a more intense electric field is formed herein. And, just as it is shown in FIG. 11 and FIG. 12, FIG. 13 shows validity in the adoption of the non-conductive coating layer (109) to the pillar-type electrode part (107).

Referring to FIG. 11 to FIG. 13, with the exception for part or, preferably, the upper part, of the pillar-type electrode part (107), the adoption of a non-conductive coating layer (109) to the remaining area including the base substrate (105) signifies the possibility of various applications of the structure by adjusting a location where the electric field is formed, a direction along which the electric field is formed, an electric field distribution, and so on.

Most particularly, according to the present invention, by adjusting the location where the non-conductive coating layer (109) is formed for the pillar-type electrode part (107), density of the pillar-type electrodes per unit surface, and so on, according to the range and intensity of the chronic pain, various output values (electrical stimulation) may be derived with the same input power value. Thus, this embodiment may be said to be very preferable in that highly intense pain may be adjusted (or relieved) without having to increase the input power value to a level that may be critical to the human body.

Figure 14:
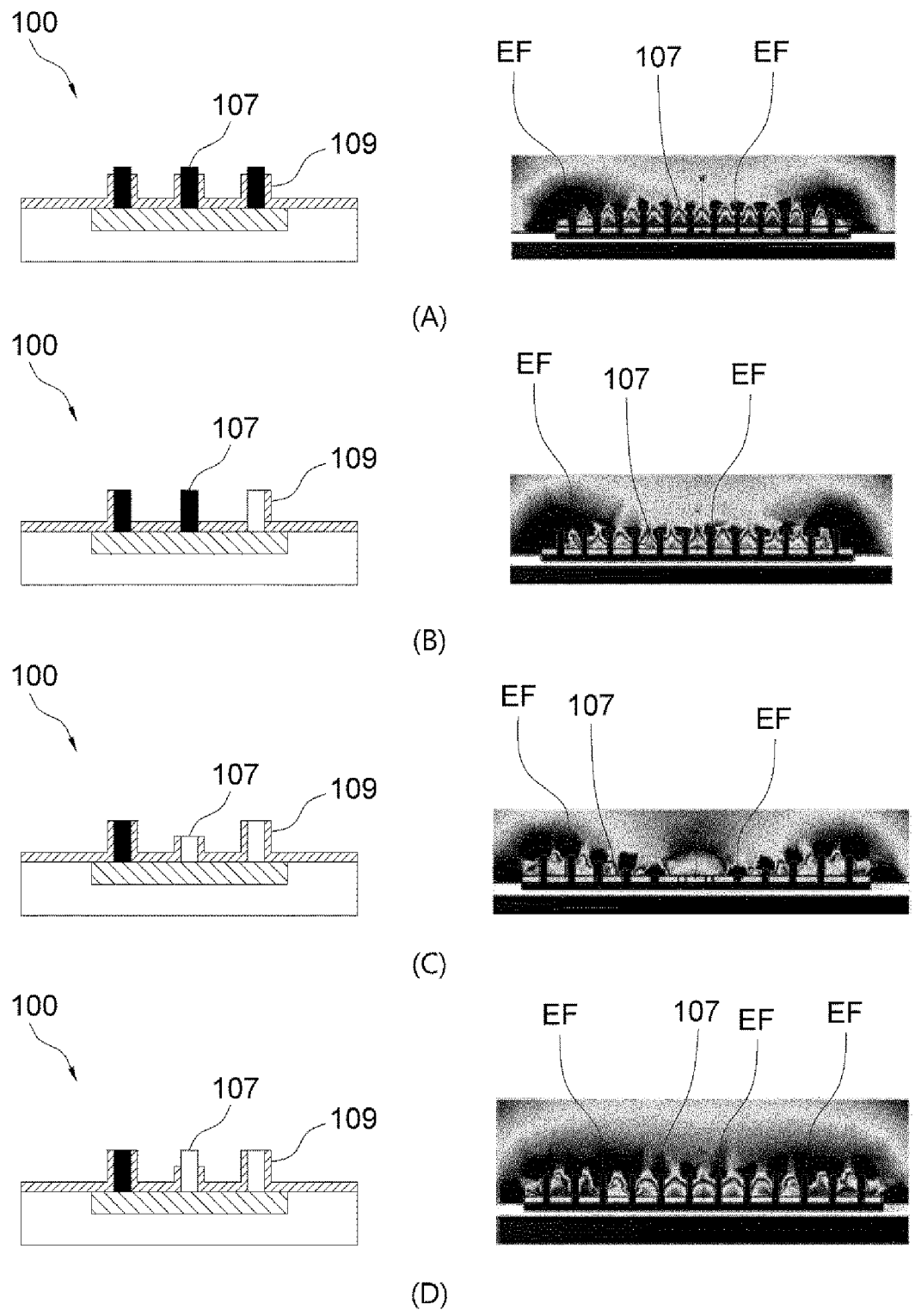
FIG. 14 is a diagram showing a non-conductive coating layer formed on a pillar-type electrode according to various embodiments of the present invention and an electric field distribution according to the respective structure.

FIG. 14 is a diagram showing a non-conductive coating layer (109) formed on a pillar-type electrode part (107) according to various embodiments of the present invention and an electric field distribution according to the respective structure. That is, the non-conductive coating layer (109) may be variously implemented, as shown in FIG. 14. And, an electric field may be formed according to the various implementations.

Figure 15:
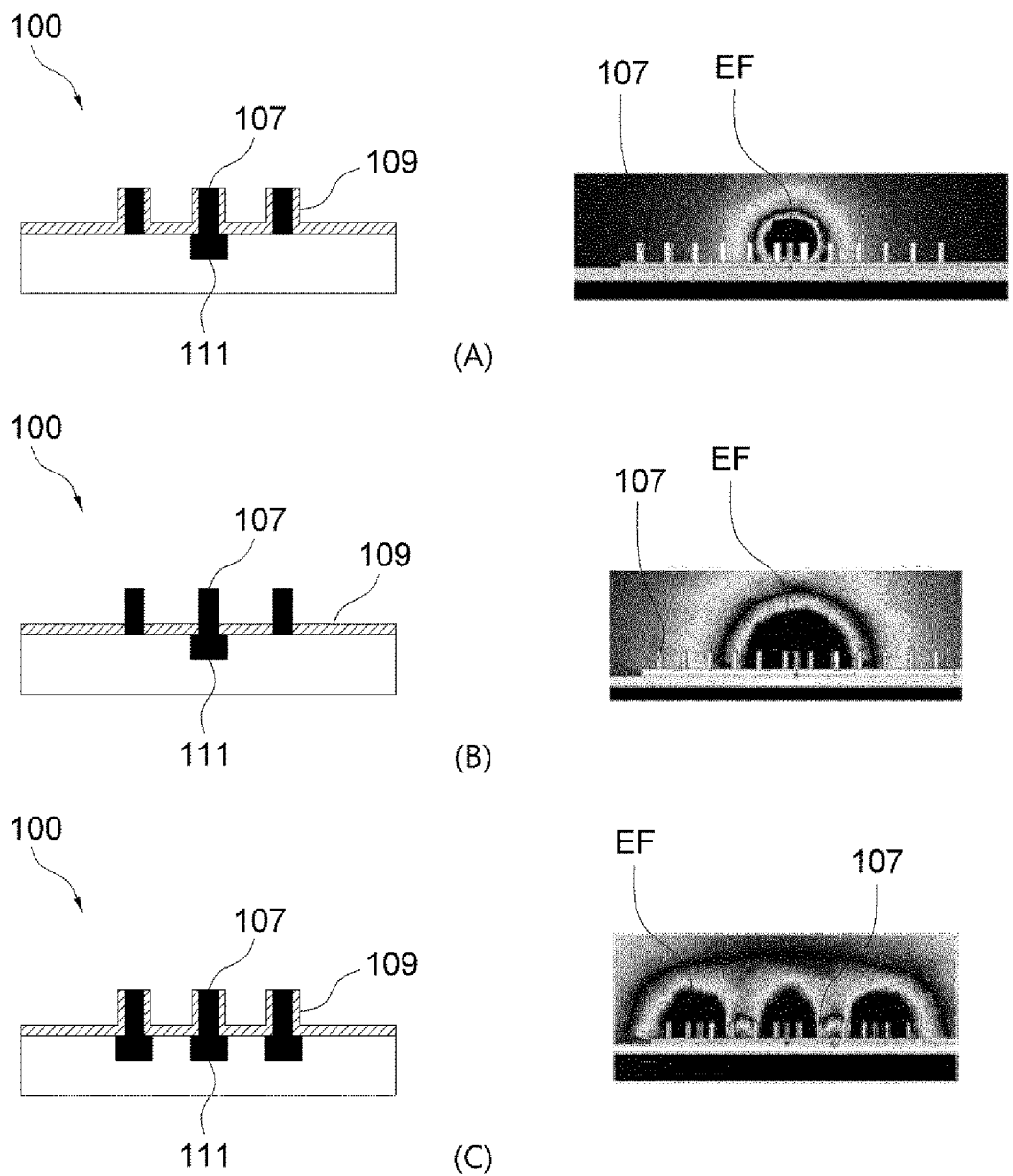
FIG. 15 is a diagram showing a non-conductive coating layer formed on a pillar-type electrode according to various embodiments of the present invention and an electric field distribution according to the respective structure, wherein a feeding is formed at a bottom part of the pillar-type electrode.

FIG. 15 is a diagram showing a non-conductive coating layer (109) formed on a pillar-type electrode according to various embodiments of the present invention and an electric field distribution according to the respective structure, wherein a feeding (111) is formed at a bottom part of the pillar-type electrode part (107). A feeding (111) may be partially formed on one or more electrodes, or a feeding (111) may be formed on all of the electrodes. In case a feeding (111) is formed on only one electrode, it has been observed that the electric field is concentrated to the one pillar-type electrode having the feeding (111) formed thereon. Therefore, the distribution of the electric field may be effectively adjusted in accordance with the location where the feeding (111) is formed.

The electric field intensity may be described as follows. The intensity of the electric field formed around each pillar-type electrode part (107) is approximately 4,000 V/m. And, herein, it has been verified through experiment that, in case feeding (111) is performed on one pillar-type electrode part (107), the electric field intensity increases to approximately 40,000 V/m, which is 10 times the intensity of the electric field formed around each pillar-type electrode part (107). Therefore, energy may be concentrated by variously adjusting the method for performing feeding (111) on the pillar-type electrode part (107).

Figure 16:
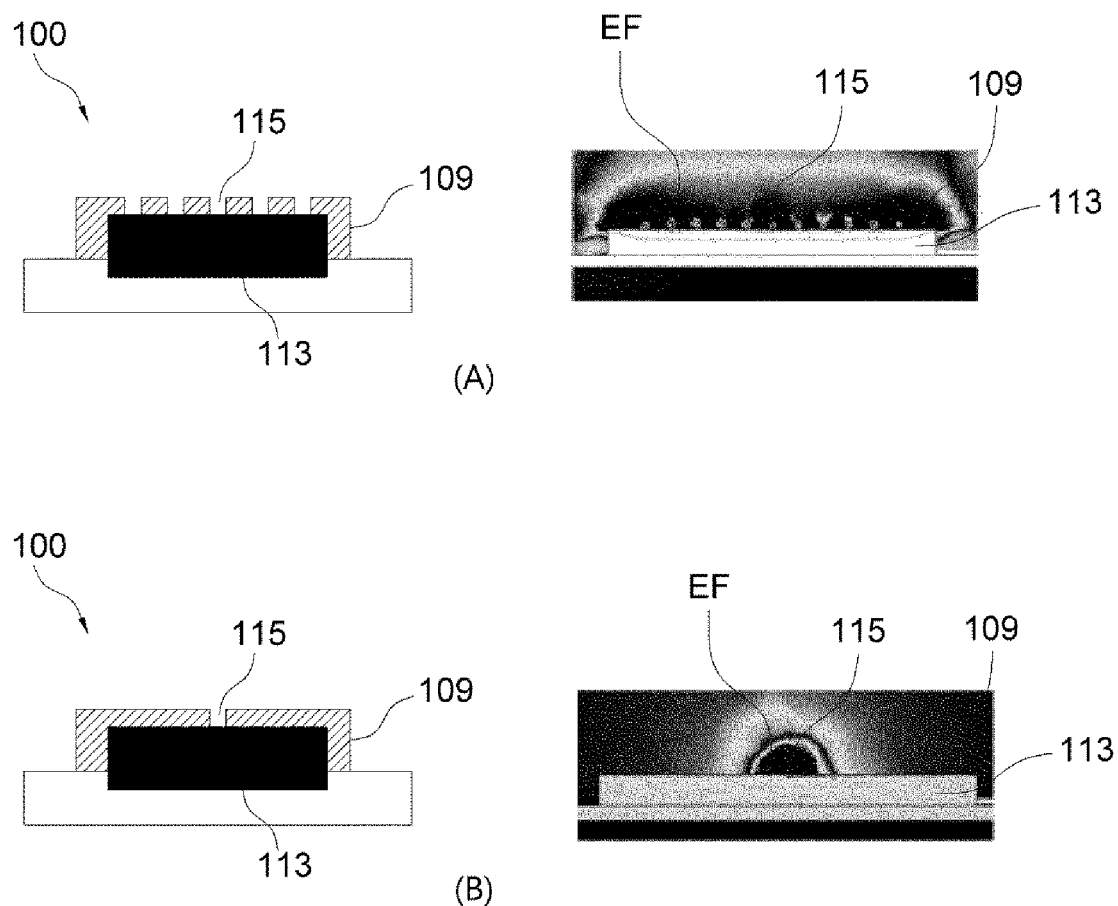
FIG. 16 is a diagram showing non-conductive coating being performed on a related art flat-type electrode and performing hole-processing on a non-conductive coating layer so as to expose the electrode according to embodiments of the present invention.

FIG. 16 is a diagram showing non-conductive coating being performed on a related art electrode part (113) and performing hole-processing on a non-conductive coating layer (109) so as to expose the electrode according to embodiments of the present invention.

As shown in the drawing, a strong electric field has been observed from the part where the hole (115) is processed. And, since the intensity or area of formation of the electric field can be adjusted according to changes in the size, location, number, and so on, of the hole(s) (115), similar results as the above-described pillar-type electrode unit (107) may be achieved. Therefore, diversity in the application is recognized in that, whenever needed, a selection may be made between a pillar-type electrode part (107) and forming a home (115) after forming a non-conductive coating layer (109) on an electrode part (113).

Figure 17:
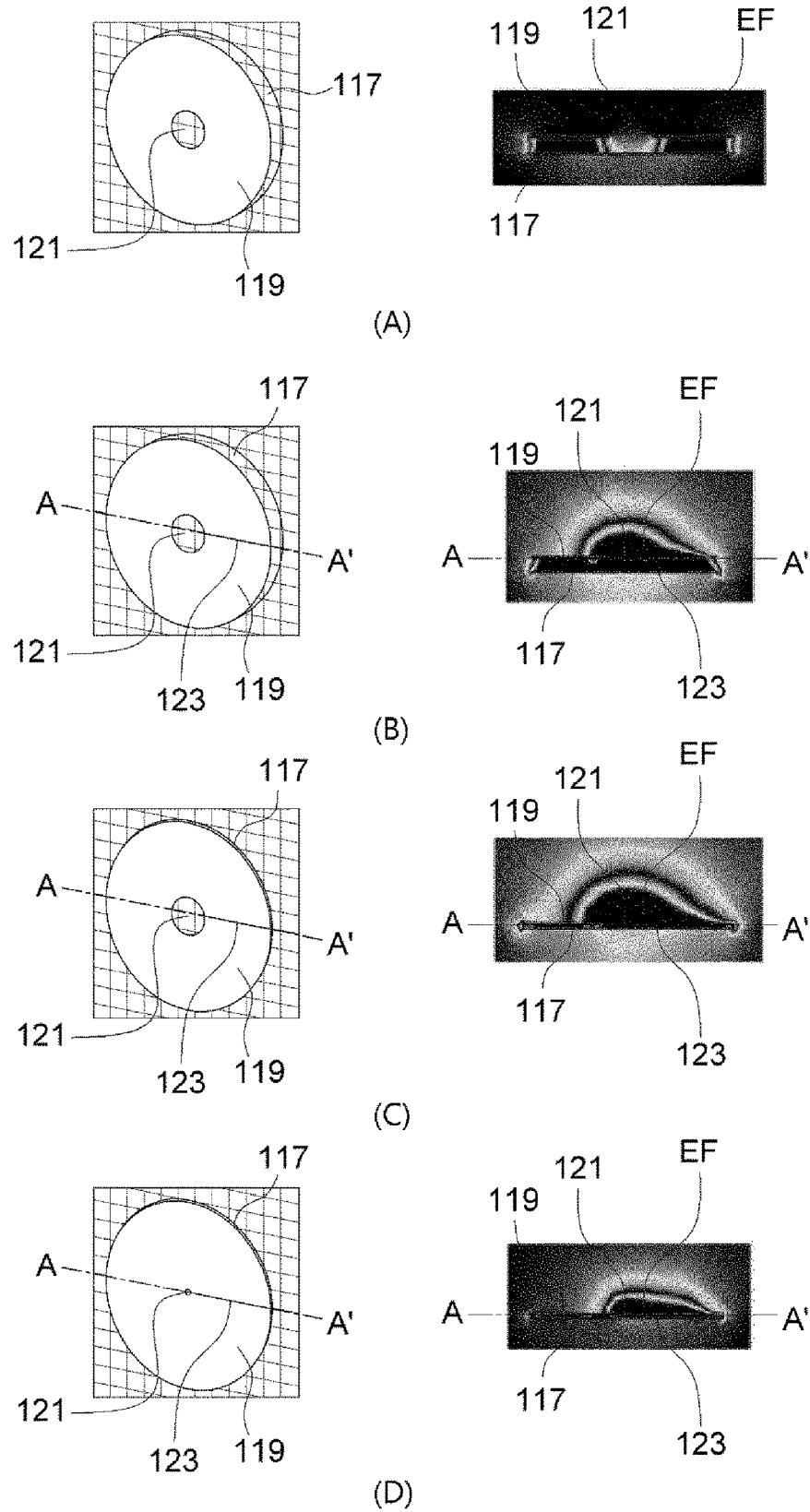
FIG. 17 is a diagram showing examples of depositing a metal plate on a coil-type electrode with a gap between the metal plate and the electrode or forming a slit on a metal plate according to various embodiments of the present invention.

FIG. 17 is a diagram showing examples of depositing a conductive plate (119) on a coil-type electrode part (117) with a gap between the conductive plate (119) and the electrode part or forming a slit (123) on a conductive plate (119) according to various embodiments of the present invention. As shown in the drawing, in case a conductive plate (119) having no slit (123) is deposited on a coil-type electrode part (117) with a gap between the conductive plate (119) and the coil-type electrode part (117), it can be known that electric field is not discharged to the outside. However, in case a slit (123) is formed, it can be verified that the electric field is discharged through the slit (123) and the hole (121). And, most particularly, it is shown that the discharge effect of the electric field through the hole (121) is noticeable. Herein, by adjusting the size of the hole (121), the gap (or distance) between the conductive layer (119) and the coil-type electrode part (117), the intensity (or force) of the electric field may be controlled.

Figure 18:
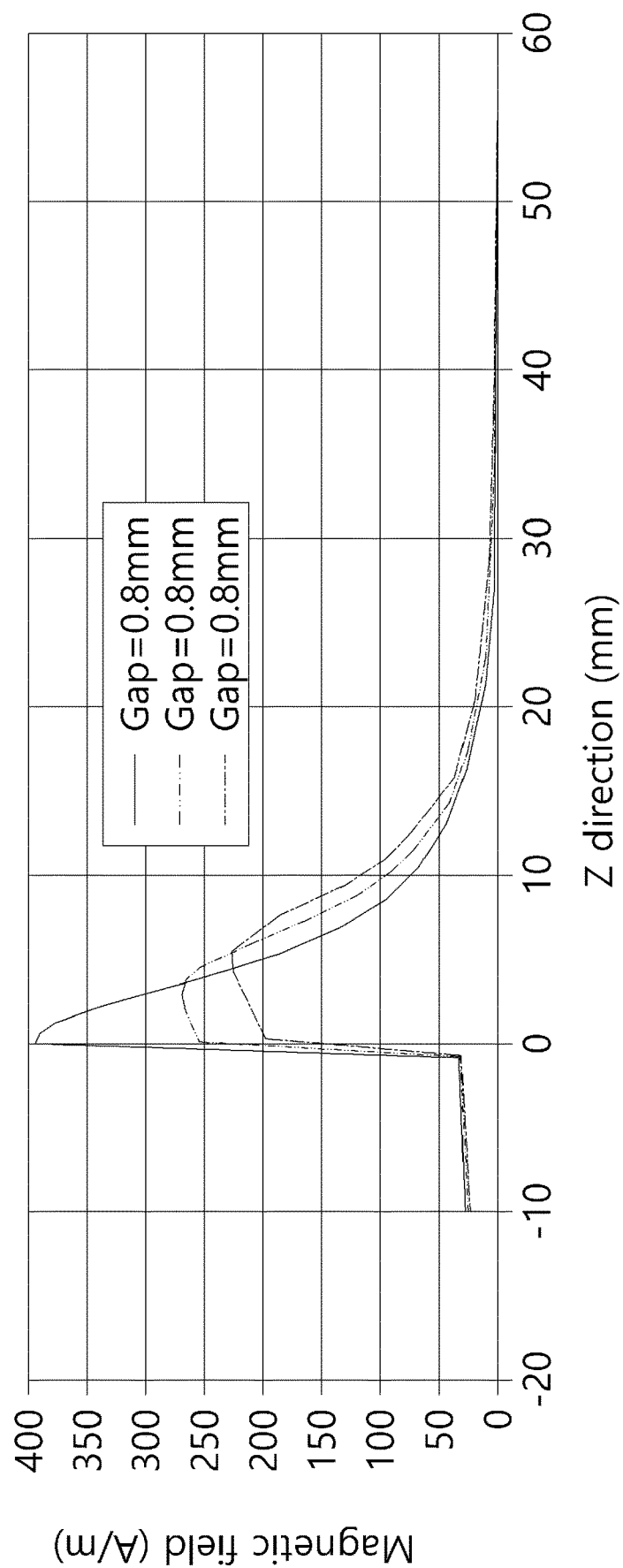
FIG. 18 is a graph comparing sizes of magnetic field energy according to a gap between the coil-type electrode and the deposited metal plate according to an embodiment of the present invention.
Figure 19:
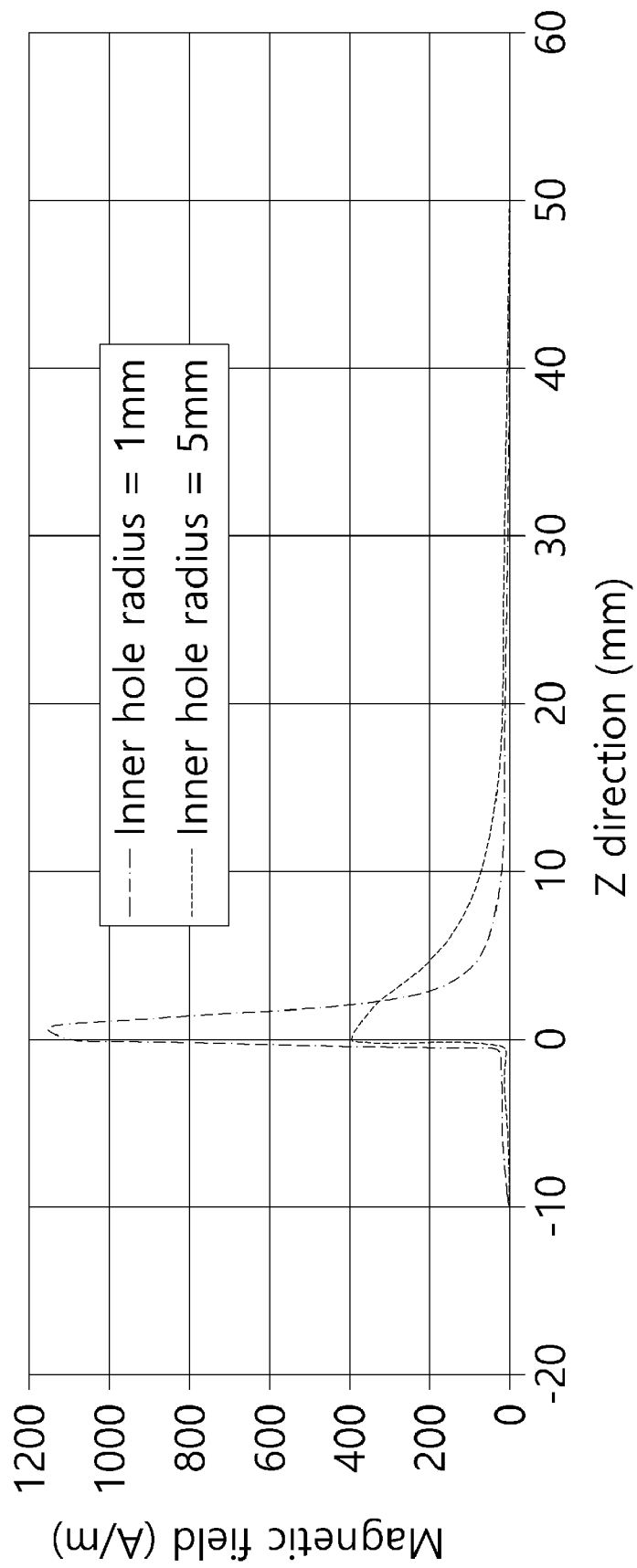
FIG. 19 is a graph comparing sizes of electric field energy according to a passthrough hole (or inner hole) size in a metal plate being deposited on a coil-type electrode according to an embodiment of the present invention.

In relation to this, as shown in FIG. 18, the intensity of the above-described electric field has been measured to be greater as the gap (or distance) between the conductive plate (119) and the coil-type electrode part (117) becomes smaller. And, as shown in FIG. 19, the intensity of the electric field has been measured to be greater as the size of the hole (115) becomes smaller.

Figure 20:
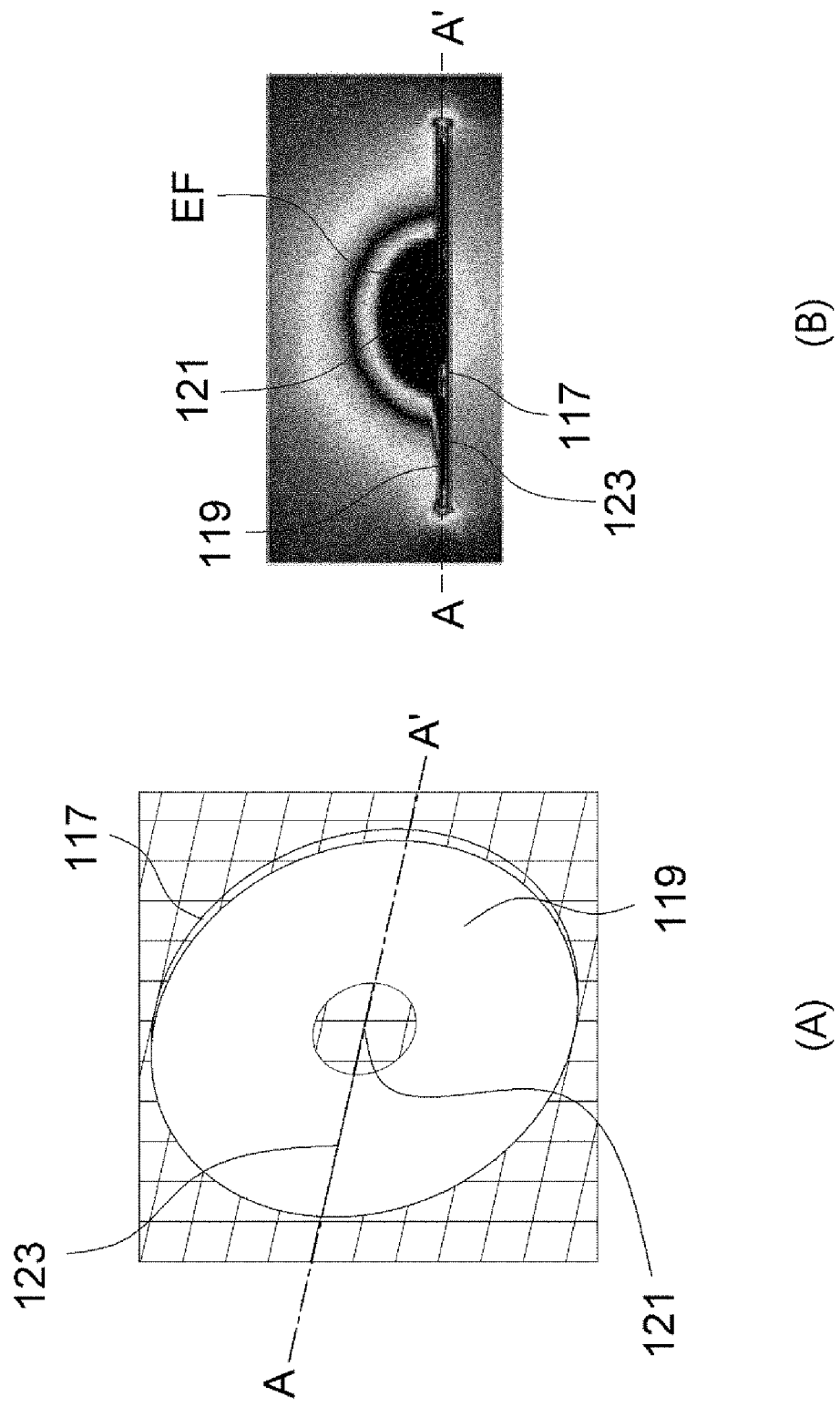
FIG. 20 is a diagram showing an example of depositing multiple metal plates on a coil-type electrode, wherein a direction of a slit formed on each metal plate is varied, according to an embodiment of the present invention.

Meanwhile, as shown in FIG. 20, multiple conductive plates (119) may be deposited on the coil-type electrode part (117) so as to be spaced apart from one another. At this point, the direction of the slit (123) may be varied. And, in this case, it has been observed that the electric field is particularly strong at a point (or position) where the hole (121) is located. That is, as a method for allowing the electric field to pass through the hole (121) region yet controlling the electric field from passing through the part where the slit (123) is formed, as described above, two conductive plates (119) may be deposited, wherein the slit (123) on each conductive plate (119) is formed along different directions. Based on the formation of the electric field, it is apparent that the electric field can only pass through the hole (121) region and that the electric field cannot pass through other regions. Thus, by allowing only the electric field of a wanted area to be passed through, the energy may be concentrated, and the region where the electric field energy is being discharged may be accurately adjusted.

Figure 21:
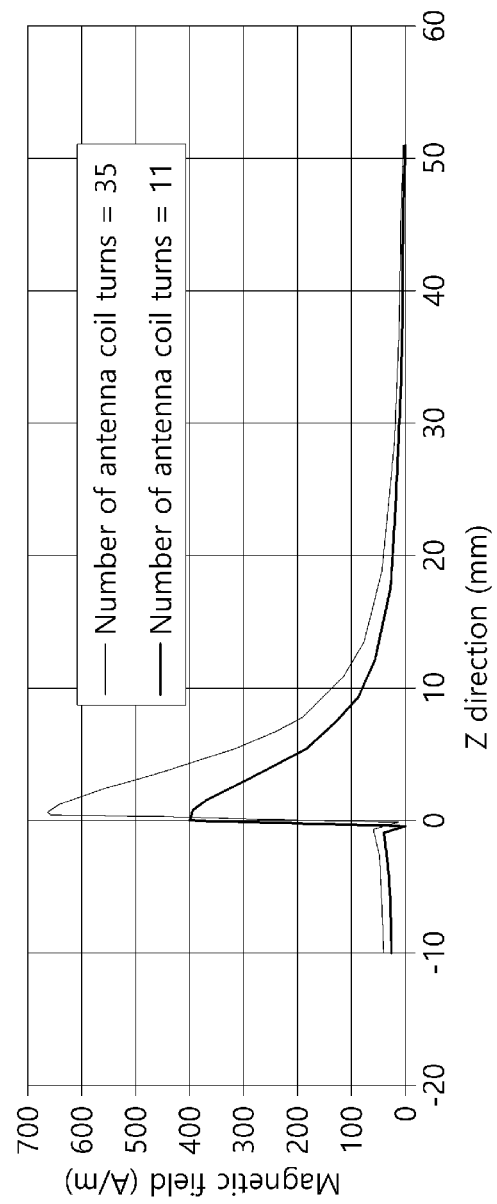
FIG. 21 is a graph comparing sizes of electric field energy according to a number of coil turns in a coil-type electrode according to an embodiment of the present invention.

FIG. 21 is a graph comparing sizes of electric field energy according to a number of coil turns in a coil-type electrode part (117) according to an embodiment of the present invention. If the number of turns is larger, since the electric field energy is concentrated, it can be verified that the size of the electric field becomes larger. Thus, by adjusting the number of coil turns, the size and region of the concentrated electric field energy may be adjusted.

<Alzheimer's Disease>

By using the stimulator according to the present invention, assessment has been made on each of the disintegration of Alzheimer's-causing protein aggregates and conformation change in Alzheimer's-causing protein oligomers. The stimulator (100) according to the present invention that is used for chronic pain and the Alzheimer's disease has the same structure and method of usage. However, since the management methods (treatment methods) of the device for diseases is specialized for each corresponding disease, the management method (or treatment method) may differ from one another.

In order to derive a parameter of an optimum power (or electric force) that is needed for disintegrating Alzheimer's-causing protein aggregates, experiments have been carried out by varying the voltage values by 50 mV, 1V, and 10V. The application time of the three different voltages was set to 1 second, and the subject protein was in an Alzheimer's-causing protein 42 (i.e., Aβ42) peptide solution incubated in distilled water (or DI water) for 8 days (see FIG. 22a).

when comparing the circular dichroism (CD) spectra of the Alzheimer's-causing protein 42 (i.e., Aβ42) peptide before and after applying the electric field (EF), with the exception for an increase in the intensity at approximately 195 nm, no particular change has been observed. Even though the intensity of the electric field does not particularly affect the CD spectrum, the feasibility of the stimulator (100) according to the present invention to influence the structure of the Alzheimer's-causing protein 42 (i.e., Aβ42) has been confirmed.

Figure 22:
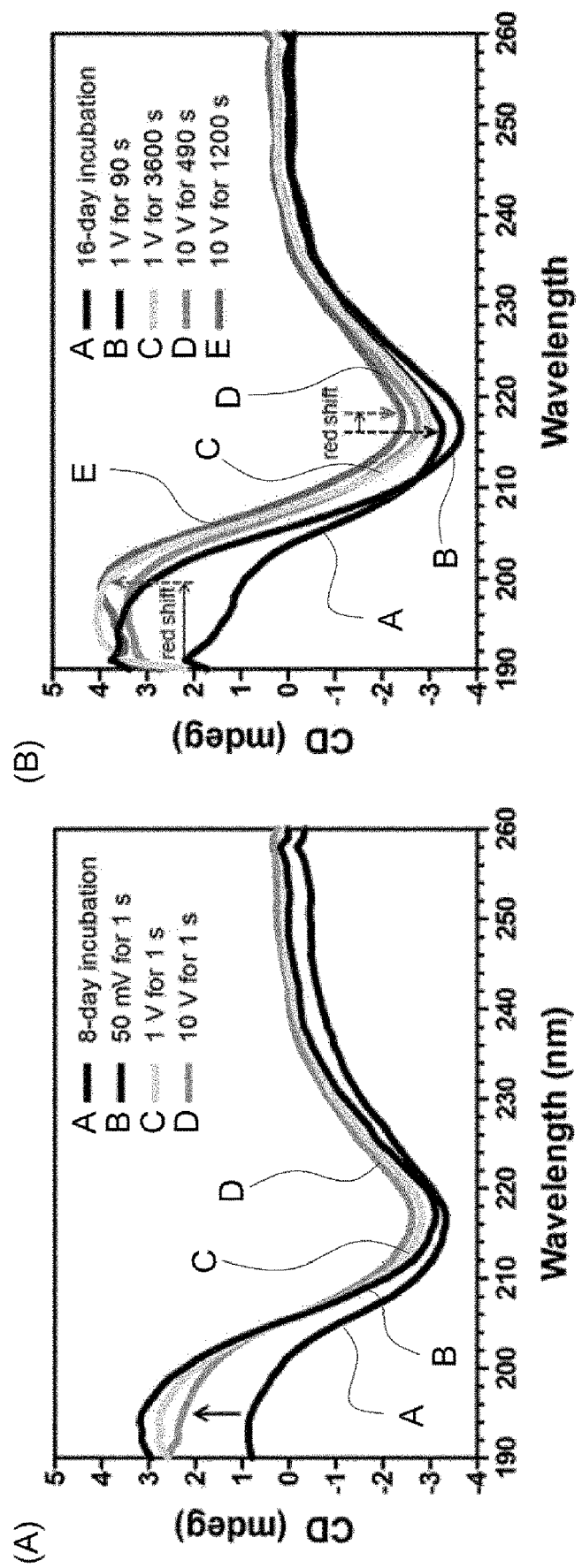
FIG. 22 illustrates CD spectrum results showing a comparison between performing electrical stimulation by varying voltage values of 50 mV, 1V, and 10V, in order to derive an optimum parameter of power (or force) that is needed for disintegrating Alzheimer's-causing protein aggregates (i.e., Aβ aggregates) using a stimulator according to an embodiment of the present invention and performing electrical stimulation using a flat-type stimulation under the same conditions.

Additionally, as shown in FIG. 22b, after applying the electric force to an Alzheimer's-causing protein 42 (i.e., Aβ42) peptide solution incubated for 16 days at four different conditions, changes in the peptide solution have been observed.

Even though predominant proportional change was not shown, in addition to a rise in the intensity at approximately 197 nm, a red-shift near 195 nm and 216 nm was observed. Results confirm that Alzheimer's-causing protein 42 (i.e., Aβ42) oligomers and amorphous aggregates, which correspond to a phase prior to maturing to a plaque-like structure, were affected by the electric field, which was applied by the stimulator (100) according to the present invention, to increase a level of beta sheet conformation.

To further investigate the effects of the stimulator (100) according to the present invention on Alzheimer's-causing protein (i.e., Aβ) conformation, conformation changes in the Alzheimer's-causing protein 42 (i.e., Aβ42) peptide structure by CD spectrum was monitored in real time. And, this was compared to an electrical stimulation system that is manufactured by using an Au film.

Figure 23:
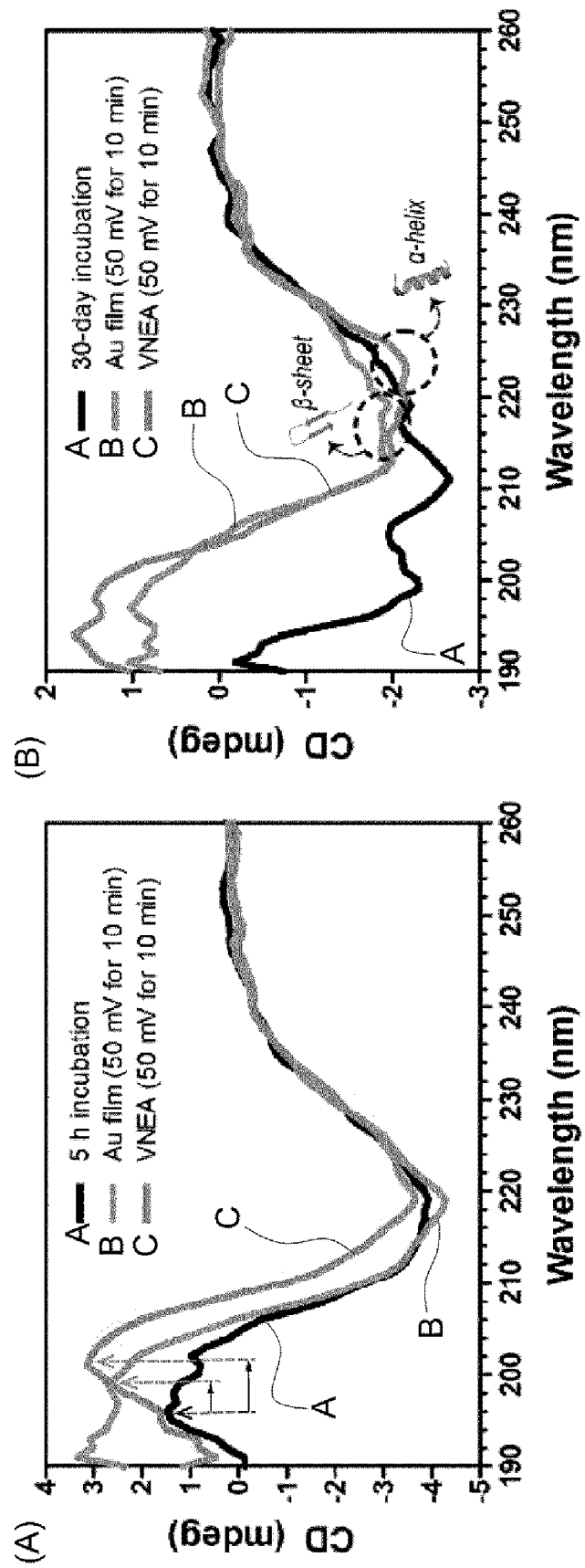
FIG. 23 illustrates CD spectrum results of monitoring conformational changes in an Alzheimer's-causing protein 42 (i.e., Aβ42) peptide structure by CD spectrum in real-time, in order to investigate influence on Alzheimer's-causing protein conformation of a stimulator according to an embodiment of the present invention, in comparison with an electrical stimulation system being fabricated with a conventional flat-type film.

As it is confirmed in FIG. 23a, when 50 mV was applied for 10 minutes to the Alzheimer's-causing protein 42 (i.e., Aβ42) peptide that had been pre-incubated for 5 hours, results confirmed that, in case of the stimulator (100) according to the present invention, beta (β)-sheet characteristic was clearly shown, whereas the stimulator (100) manufactured by using an Au film showed a slower conversion to beta (β)-sheet.

Meanwhile, in FIG. 23b, it has been confirmed that, in case of applying the same electric field as FIG. 23a to the Alzheimer's-causing protein 42 (i.e., Aβ42) peptide that is incubated for 30 days, the Au film stimulator (100) converted the Alzheimer's-causing protein 42 (i.e., Aβ42) peptide from an amorphous (or unstructured) form to beta (β)-sheet. And, conversely, the stimulator (100) according to the present invention showed a distinct negative band at approximately 222 nm indicating a transition to α-helix, which is generally shown in a Tetrafluoroeethylene (TFE) condition. Therefore, the results of the two different types of stimulators (100) are clearly distinguished from one another.

Herein, it may be interpreted that insoluble plaque-like structures intensively undergo (or suffer) high intensity multidirectional local electric field while precipitating, whereas the dispersed soluble oligomers are less affected by the electric field. Furthermore, the stimulator (100) according to the present invention showed feasibility of transition to an α-helical structure. Since the disaggregated Alzheimer's-causing protein 42 (i.e., Aβ42) peptide has re-aggregated strongly within a short period of time, this result was only observed with an electric field system (electrical stimulation device) being applied to a living body. This result is consistent with previous theoretical demonstrations of a close correlation between Alzheimer's-causing protein conformation and electric field.

It shall be noted that the embodiments set forth herein are provided to describe the embodiments according to the present invention, and not to limit the present invention. Furthermore, it may be understood by anyone with ordinary skills in the field that other various embodiments may also be implemented without deviating from the technical scope and spirit of the present invention.

| Description of reference numerals | |
|---|---|
| 100 : stimulator | 101 : controller |
| 103 : substrate | 105 : base substrate |
| 107, 113, 117: electrode part | 109 : non-conductive coating layer |
| 111 : feeding | 115 : hole |
| 119 : conductive plate | 121 : through hole |
| 123 : slit | |

What is claimed is:

1. A stimulating device being equipped with an electrode element recording and stimulating nerve signals for diagnosis and treatment of chronic pain or Alzheimer's disease, wherein the stimulating device provides electrical stimulation for chronic pain or Alzheimer's-causing proteins or measures bio signals, the stimulating device comprising:
   a controller;
   a substrate being coupled to a bottom of the controller, and having a wireless power receiving and signal delivering electrode being mounted thereon as a single body or being distinctively mounted thereon, wherein the wireless power receiving and signal delivering electrode is configured to wirelessly receive power and wirelessly deliver bio signals; and
   an electrode element being coupled to a bottom of the substrate and being configured to deliver electrical stimulation to tissues inside a body,
   wherein the electrode element comprises:
      a base substrate; and
      at least one pillar-type electrode part protruding from the base substrate,
   wherein the at least one pillar-type electrode part is configured to be inserted into the tissues to deliver the electrical stimulation,
   wherein a non-conductive coating layer is formed on an entire portion of a side surface of the pillar-type electrode part.

2. The stimulating device of claim 1, wherein a feeding is formed in a region where at least one bottom part of the pillar-type electrode part is embedded in the base substrate.

3. The stimulating device of claim 1, wherein an edge portion of the pillar-type electrode part and a portion of the side surface of the pillar-type electrode part are exposed.

4. The stimulating device of claim 1, wherein the substrate is distinguished as a substrate including a power receiving electrode capable of wirelessly receiving power, and a substrate including a signal transmitting electrode capable of wirelessly delivering bio signals.

\* \* \* \* \*